United States Patent [19]

Overton et al.

[11] Patent Number: 5,611,846
[45] Date of Patent: Mar. 18, 1997

[54] PORTABLE GAS CHROMATOGRAPH

[75] Inventors: Edward B. Overton; Kenneth R. Carney, both of Baton Rouge, La.

[73] Assignee: Board of Supervisors of Louisiana State University and Agricultural and Mechanical College, Baton Rouge, La.

[21] Appl. No.: 684,332

[22] Filed: Jul. 19, 1996

Related U.S. Application Data

[63] Continuation of Ser. No. 563,558, Nov. 28, 1995, abandoned, which is a continuation of Ser. No. 181,705, Jan. 14, 1994, abandoned.

[51] Int. Cl.$^6$ .......................... B01D 15/08; B01D 53/30
[52] U.S. Cl. .......................... 96/102; 73/23.36; 73/23.41; 73/23.42; 95/82; 95/86; 95/87; 96/104; 96/105
[58] Field of Search .................. 96/101, 102, 103, 96/104, 105, 106; 95/82, 83, 87, 84, 86; 73/23.35, 23.36, 23.39, 23.41, 23.42

[56] References Cited

U.S. PATENT DOCUMENTS

| | | | |
|---|---|---|---|
| 3,053,077 | 9/1962 | Tracht | 96/106 |
| 3,062,039 | 11/1962 | Ayers | 95/87 |
| 3,366,149 | 1/1968 | Taft et al. | 96/105 |
| 3,537,585 | 11/1970 | Waters | 96/106 |
| 3,668,834 | 6/1972 | Deans | 95/89 |
| 4,269,608 | 5/1981 | Sisti et al. | 55/67 |
| 4,650,964 | 3/1987 | Vincent | 95/87 |
| 4,728,776 | 3/1988 | Vincent | 95/87 |
| 4,805,441 | 2/1989 | Sides et al. | 95/87 |
| 4,948,389 | 8/1990 | Klein et al. | 95/87 |
| 5,005,399 | 4/1991 | Holtzclaw et al. | 73/23.39 |
| 5,014,541 | 5/1991 | Sides et al. | 73/23.41 |
| 5,028,243 | 7/1991 | Rubey | 95/87 |
| 5,047,073 | 9/1991 | Stetter et al. | 95/82 |
| 5,048,322 | 9/1991 | Hiller et al. | 73/23.41 |
| 5,096,471 | 3/1992 | Sacks et al. | 95/87 |

(List continued on next page.)

OTHER PUBLICATIONS

Klemp et al., "Cryofocusing Inlet with Reverse Flow Sample Collection for Gas Chromatography," Anal. Chem., vol. 65, pp. 2516–2521 (1993).

Müller et al., "Column–Switching in Capillary Gas Chromatography," Siemens Analytical Application Note 297, Siemens AG, Karlsruhe, Germany (1981).

"Sentex Portable Gas Chromatographs" (Product Brochure, date unknown).

Müller et al., "New Horizons in High Performance Gas Chromatography Using a Live–Controlled Column–Switching System," Siemens Analytical Application Note 282, Siemens AG, Karlsruhe, Germany (date unknown).

K.R. Carney et al., "Use of a Microchip Gas Chromatograph for Ambient Air Analysis," chap. 2 in E.D. Winegar et al. (eds.), *Sampling and Analysis of Airborne Pollutants*.

E.B. Overton et al., "Microchip Gas Chromatograph with In–Line Sample Concentration Suitable for Use with Ion Mobility Spectrometry," final report submitted to Krug Life Sciences, Jun. 21, 1991.

*Primary Examiner*—Jay H. Woo
*Assistant Examiner*—Duane S. Smith
*Attorney, Agent, or Firm*—John H. Runnels

[57] ABSTRACT

Gas chromatographs are disclosed that may be constructed to be portable, light, rugged, fast, sensitive, and to use only utilities (compressed gas and electricity) that are readily available in the field. The gas chromatographs can also perform novel extractions of analytes from gaseous, liquid, or solid samples. The chromatographs can be truly portable; they can operate with approximately 100 watts of power (at peak power consumption); and they are extremely fast. The chromatographs are not limited just to portable applications, but will also find many uses within laboratories, because they require minimal laboratory bench or other space, because they can operate at high speed, and because they can operate with minimal consumption of utilities (compressed gases, air conditioning, etc.).

34 Claims, 10 Drawing Sheets

U.S. PATENT DOCUMENTS

| | | | |
|---|---|---|---|
| 5,098,451 | 3/1992 | Rounbehler et al. | 55/67 |
| 5,099,743 | 3/1992 | Rounbehler et al. | 86/50 |
| 5,108,705 | 4/1992 | Rounbehler et al. | 422/89 |
| 5,114,439 | 5/1992 | Yost et al. | 55/20 |
| 5,141,532 | 8/1992 | Sacks et al. | 96/102 |
| 5,152,176 | 10/1992 | Bryselbout et al. | 95/87 |
| 5,215,556 | 6/1993 | Hiller et al. | 95/87 |
| 5,224,972 | 7/1993 | Frye et al. | 95/87 |
| 5,268,302 | 12/1993 | Rounbehler et al. | 436/96 |
| 5,300,758 | 4/1994 | Rounbehler et al. | 219/497 |
| 5,310,681 | 5/1994 | Rounbehler et al. | 436/106 |

PORTABLE GAS CHROMATOGRAPH

The development of this invention was partially funded by the Government through a subcontract under Prime Contract DNA001-91-C-0146 with the Defense Nuclear Agency. The Government may have certain rights in this invention.

This application is a continuation of application Ser. No. 08/563,558, filed Nov. 28, 1995 now abandoned, which is a continuation of application serial number 08/181,705, filed Jan. 14, 1994 now abandoned.

This invention pertains to improvements in gas chromatographs, particularly to improvements increasing the portability and versatility of gas chromatographs.

A gas chromatograph (GC) is an analytical instrument that takes a gaseous sample (or converts a sample to the gaseous state if necessary), and separates the sample into individual compounds, allowing the identification and quantification of those compounds. The principal components of a typical gas chromatograph are the following: an injector that converts sample components into gases (if necessary), and that moves the gases onto the head of the separation column in a narrow band; a separation column (typically a long, coiled tube) that separates the sample mixture into its individual components as they are swept through the column by an inert carrier gas, the separation being based on differential interactions between the components and an immobilized liquid or solid material within the column; a detector that detects and measures components as they exit the separation column; and a data display.

Typical modern GC instruments are configured with a heated-block "flash evaporator" type injector, a long capillary tube column (e.g., 0.3 mm ID×30 meters long), an oven housing the column to maintain and to change the column's temperature in a predictable and reproducible fashion, a flame ionization detector (or other type of detector), and a computer with dedicated hardware/software to process the data collected. Conventional GC instrumentation can be modified by using different columns (different lengths, different inner diameters, different sorbent phases, and different phase thicknesses); different detectors; and different data management systems. Conventional units are typically about the size of a large microwave oven (50–100 kg), require 2 to 3 kilowatts of power and considerable air conditioning, and with their accessories occupy six or more linear feet of laboratory bench space.

Conventional gas chromatographs are relatively bulky, and although they are suitable for use in a laboratory, they are difficult to use in portable applications. There is a great need for improved portable gas chromatographs. A truly portable, easy-to-operate gas chromatograph would have many applications. The ability to easily analyze samples in the field would find numerous uses in environmental work, industrial plants, and in many other areas where the uses of portable gas chromatography cannot easily be envisioned. A few portable gas chromatographs are currently available, but the currently available, battery-operated units are limited to analysis of volatile compounds (those having an ambient temperature vapor pressure greater than about 1 mm of mercury), because reliance on a battery power supply has limited their heating capacities. Currently available portable GC's do not have heated injector or detector zones, and do not support true temperature programming (as opposed to ballistic heating). One model currently available commercially from MTI Analytical Instruments uses microbore columns.

There is a continuing need for a truly portable, inexpensive, and versatile gas chromatograph.

Hiller et al., U.S. Pat. No. 5,048,322 discloses a large volume injection gas chromatographic method in which the temperature of the column inlet and of the analytical column are separately controlled, or in which the temperature of a retention gap and the temperature of the analytical column are separately controlled. By heating the inlet before heating the column, nonvolatile analytes could be concentrated in the column, improving the observed signal-to-noise ratio.

Sisti et al., U.S. Pat. No. 4,269,608 discloses a gas chromatographic method in which the injection zone and an initial portion of the column are kept at a low temperature, followed by a quick temperature change at the end of the initial portion of the column. Cooling was preferably performed by the flow of a cooling fluid outside the injector and column, while heating was controlled by an oven housing the column.

Rubey, U.S. Pat. No. 5,028,243 discloses a method for reconcentrating a sample with a column having a negative thermal gradient, a thermal gradient that may vary as a function of time. Heating and cooling are accomplished by placing the column in a sheath in which there is a resistance heating element, and in which heated or cooled fluids may flow, either co-current or counter-current to the sample flow. The column and temperature control means possess a low temperature inertia so that the column rapidly responds to heating or cooling.

Yost et al., U.S. Pat. No. 5,114,439 discloses a method of gas chromatography in which direct resistive heating of the column is used to control its temperature. With a low-thermal-mass column and conductive coating, temperature changes were said to be readily effected.

Klemp et al., "Cryofocusing Inlet with Reverse Flow Sample Collection for Gas Chromatography," Anal. Chem., vol. 65, pp. 2516–2521 (1993) (not admitted to be prior art) describes a cryofocusing inlet system for a gas chromatograph. The gas flow direction through a metal capillary cryofocusing tube is reversed after sample collection so that the sample injection onto the column occurs from the downstream end of the cryofocusing tube.

Müller et al., "New Horizons in High Performance Gas Chromatography Using a Live-Controlled Column-Switching System," Siemens Analytical Application Note 282, Siemens AG, Karlsruhe, Germany (date unknown) discloses a method of gas chromatography using real-time column switching for various purposes. See also Müller et al., "Column-Switching in Capillary Gas Chromatography," Siemens Analytical Application Note 297, Siemens AG, Karlsruhe, Germany (1981).

"Senrex Portable Gas Chromatographs" (Product Brochure, date unknown) describes portable gas chromatographs currently being offered commercially. The oven and column are conventional in nature, albeit somewhat smaller than usual. Temperature programming is not supported. This model also offers a bolt-on concentrator option.

Previous work from the laboratory of the present inventors is reported in K. R. Carney et al., "Use of a Microchip Gas Chromatograph for Ambient Air Analysis," chap. 2 in E. D. Winegar et al. (eds.), *Sampling and Analysis Airborne Pollutants*; and in E. B. Overton et al., "Microchip Gas Chromatograph with In-line Sample Concentration Suitable for Use with Ion Mobility Spectrometry," final report submitted to Krug Life Sciences, Jun. 21, 1991; neither of these two documents from the inventors' own laboratory is admitted to be prior art.

Novel methods and apparatus for gas chromatography have been discovered. Gas chromatographs in accordance with the new invention may be constructed to be portable, light, rugged, fast, sensitive, and to use only utilities (compressed gas and electricity) that are readily available in the field. The novel gas chromatographs perform the same functions as do conventional GC's. They can also perform novel extractions of analytes from gaseous, liquid, or solid samples. The novel chromatographs can be truly portable, as they can be made much smaller than conventional chromatographs; they can operate with approximately 100 watts of power at peak power consumption, preferably with a heater consuming less than about 50 watts at peak consumption; and they are extremely fast. The novel chromatographs are not limited just to portable applications, but will also find many uses within laboratories, because they require minimal laboratory bench or other space, because they can operate at high speed, and because they can operate with minimal consumption of utilities (compressed gases, air conditioning, etc.).

The novel chromatograph, which can combine the functions of extraction from a sample and GC analysis of that sample into a single compact unit, can not only perform all the functions of conventional GC analysis, but will also open up many new analytical applications that have not previously been envisioned due to the size, cost, slowness, and complexity of conventional GC instrumentation. Just as small, dedicated personal computers opened up many new applications and commercial products that were not possible using work stations or mainframe computers, the novel chromatograph will open up many new analytical applications that are not feasible with conventional GC instrumentation.

The subsystems of the invention (some of which are optional) include the following: a sample processing module (SPM) that extracts and converts analytes into the gaseous phase; an interface module (IM) between the extractor/injector and the analyzer that transmits gaseous analytes to the analyzer module in a narrow band, controls carrier gas and make-up gas flows and pressures, and controls back-flushing functions; an analyzer module (AM) using very high-resolution, small inner diameter columns, a low-thermal-mass column heating source, a low-flow detector, and control electronics and pneumatics to produce very fast, high resolution gas chromatograms of either volatile or semivolatile analytes (those having retention indices of 100 to 3000, or higher), or having both volatile and semivolatile analytes; and a data processing module (DPM) that converts electrical signals into useful information, and that can solve problems related to specific applications (e.g., identity and concentration of sample components). By comparing measurements to those of known compounds, the DPM can indicate the likely identity of compounds exiting the column; by cross-checking with measurements from different columns, a higher degree of certainty in the identification is possible. The strength of the signal versus the strength of the signal from a known amount of a standard is a measurement of the concentration of the compound. Thus the instrument can act more as a complete analyzer of a mixture than will a typical stand-alone GC.

The novel gas chromatographs can be constructed relatively inexpensively (when compared to the cost of conventional GC's), with a small size and low weight. They can operate with little power and low consumption of laboratory space/utilities, and are rapid and easy to use.

Among the features and advantages (some of which are optional) that may be achieved with the novel gas chromatographs are the following:

Heat is only applied to those areas through which the samples or analytes pass, allowing for a system of low thermal mass. "Low thermal mass" refers to the ability of the column and other components to undergo relatively rapid temperature changes (both heating and cooling) in the environment of the chromatograph. More specifically, the column should be capable of a controlled, or programmed temperature rate of change of at least 0.5° C. per second heating, and at least 1° C. per second cooling; more preferably capable of controlled rates of at least 10° C. per second heating, and at least 20° C. per second cooling; and most preferably capable of controlled rates of at least 25° C. per second heating, and at least 25° C. per second cooling.

Thermal stability is achieved by rapid feedback and control through a microprocessor (e.g., at a rate of about 100 Hz), without the need for a temperature controller separate from the microprocessor. Prior GC's have generally had a separate temperature controller, and have achieved thermal stability only by having a high thermal mass, which limits the rate of controlled temperature programming possible.

A chromatograph in accordance with the present invention can analyze both volatiles and semivolatiles in a single analytical run. By contrast, currently available portable GC's do not have this capability. While analysis of both volatiles and semivolatiles in a single run is possible on current laboratory-bench scale GC's, such an analysis would require much greater power consumption and significantly longer times than are required through the use of a chromatograph in accordance with the present invention.

Heat may be applied only during those times when, and those places where, analytes or samples are traversing particular zones. The placement of the heating element close to the column minimizes undesirable "cold spots" on the column.

Temperature sensors in intimate contact with the heated zones provide rapid feedback. Rapid feedback permits highly accurate and reproducible temperature control and temperature programming. Controlled temperature programming, i.e. temperature programming following a precisely-defined course over time, may be achieved through microprocessor control of the heating.

The extraction and injection functions may be combined into a single, low-thermal-mass module, the sample processing module (SPM).

The extraction and injection functions module (the SPM) may be "multidimensional," i.e., separate hardware components may be used for different extraction/injection operations, depending on the specific application (e.g., gases in air, volatiles in air, volatiles in aqueous samples, volatiles in solid samples, semivolatiles in air or on filters, semivolatiles in organic solvents, semivolatiles in aqueous samples, semivolatiles in solid samples, etc.) These hardware components may be modular, so that they may be easily replaced. Also, several such components may be mounted simultaneously via connections in the interface module, with particular components selected for use by the controller.

Microprocessor control of temperatures, sample pumps, gas flows, gas pressures, and valve pneumatics may be used to extract/inject various analytes via the SPM.

Low thermal mass, short, open tubular columns, with precise temperature control of the tubes, and with different wall coating materials (e.g., deactivated surfaces, various liquid phases, various porous layers) and/or similar bulk packing materials may serve as the extractor-flash evaporator/injector for various analyte/sample matrix combinations.

The SPM may use multiple, low-thermal-mass temperature zones, under microprocessor control, to achieve the extractor/injector functions.

The IM may use temperature, pressure, or flow control or programming to transmit analytes from the SPM to the AM in a narrow band.

The IM may use an open tubular retention gap interface connection between the SPM and the AM. Valving and electrical circuits and connectors can be fabricated with silicon micromachining technology.

The AM may use very rapid and reproducible temperature programming, with low thermal mass ovens and intimate contact with temperature sensors, as well as real-time control with microprocessors, to achieve "ambient temperature cryofocusing" over a wide range of analyte volatilities. "Cryofocusing" is the concentration of analytes by condensing them out of their original gas matrix into a smaller volume in an inert tube, such as a tube made from stainless steel. In the past, cryofocusing has typically been accomplished by cooling the sample gas stream to liquid nitrogen temperatures. The analytes can then be transferred to the column by flash heating. Often, the sample is then "refocused" at the head of the column. By using sorbent materials in a trap, a similar effect can be achieved with trapping at ambient temperatures. Thus this effect may considered a type of "ambient temperature cryofocusing." More conventional cryofocusing temperatures may also be used in situations where a suitable coolant (e.g., liquid nitrogen) is available.

The AM may use pressure or flow programming of the carrier gas to speed analysis times, and to maintain chromatographic resolution.

Deans switching or equivalent pressure/flow alterations, or temperature alterations, may be used in the IM or AM to select appropriate combinations of analytical columns and detectors for specific applications.

Detectors may be designed for low flow of carrier and make-up gases, and with low thermal masses, to minimize power and compressed gas consumptions. Sequential detectors of different types may also be used to increase the information available from an analysis run.

All modules and their functions are designed for real-time control with dedicated microprocessors to integrate the various subcomponents into an effective analytical extractor/analyzer instrument package.

A breadboard prototype embodiment of a portable gas chromatograph in accordance with the present invention has been constructed and successfully operated. The breadboard embodiment was capable of analyzing volatile and semivolatile compounds having ambient temperature vapor pressures as low as $2 \times 10^{-5}$ mm Hg. A heated injection system for introducing air samples was used, in which samples were loaded by means of a small vacuum pump placed downstream of the sample flow path, which included the sample loop. The injector temperatures could be as high as 255° C. The chromatographic column assembly comprised a 3 meter, 0.100 mm iod., open tubular column with a heater and a resistance temperature detection (RTD) sensor in intimate contact with the column. The temperature sensor wire was threaded inside a thin-walled, electrically-heated metal tube. Gas flow down the length of the tube promoted even heating of the column, also contained within the tube. The column assembly was housed in a rigid, alumina-silica thermal insulator. The column heater could be temperature programmed at controllable rates up to 5° C. per second at temperatures up to 230° C. Even higher rates could be achieved at lower temperatures. A temperature programming rate of 5° C. per second at 230° C. required approximately 110 watts of power. Temperature programming over the same temperature range at a rate of 1° C. per second required about 40 watts of power. A cooling fan activated by the electronic control board helped cool the column after heating. Pressure programming of the carrier gases was also possible.

The three principal heated zones of the chromatograph were a heated injector, a thermally desorbable sorbent-tube trap for sample preconcentration at a sampling rate up to about 1 L/min, and a temperature-programmable oven. Electronic control circuitry provided on-board microprocessor control of the temperature in all three zones, as well as of the temperature in the detector zone. The microprocessor control also maintained the carrier gas pressure at the column head, and managed the flow of sample and carrier gas through the entire system by appropriate sequencing of flow control valves. All control parameters were adjustable electronically from a controlling terminal, or through interface software.

The Injector

Figure 5:
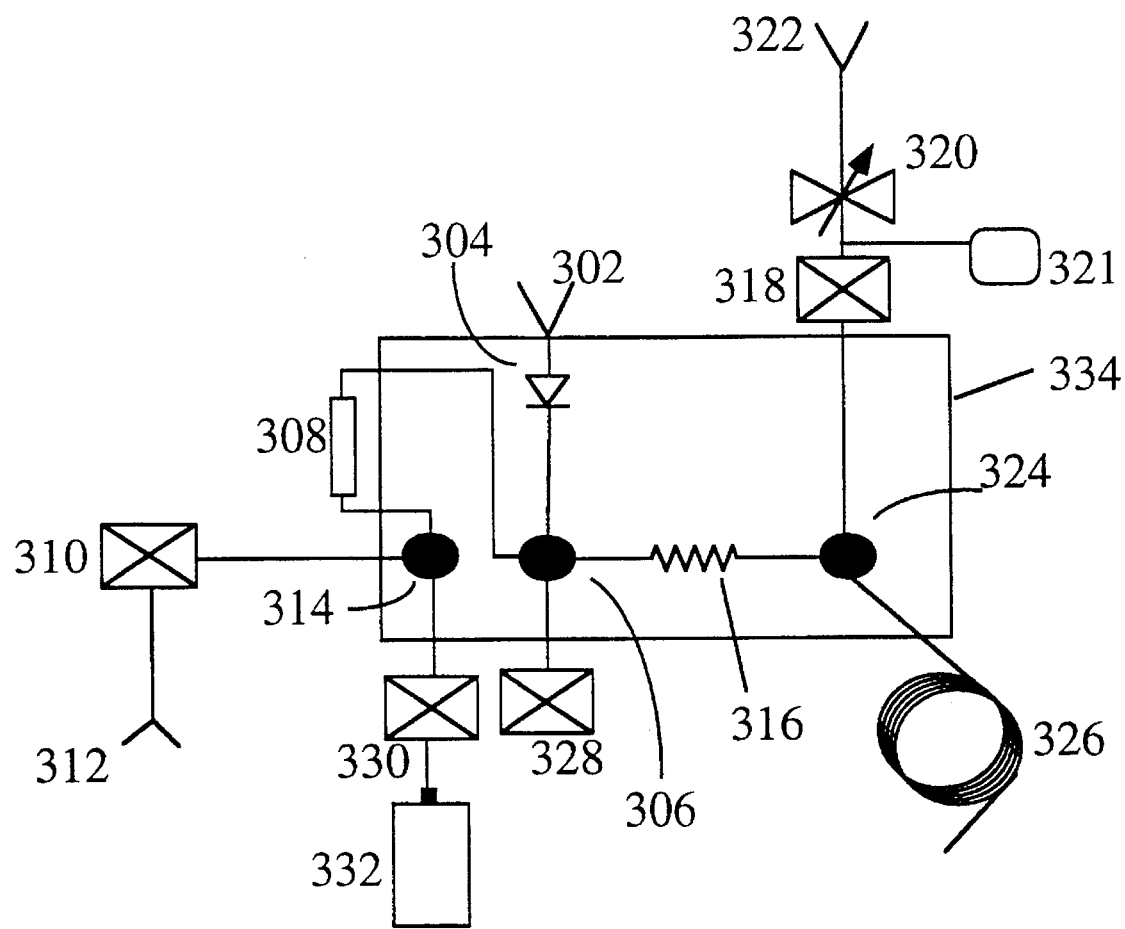
FIG. 5 illustrates schematically the injector assembly in the single automatic gas phase inlet configuration.

All components of the injector were temperature-rated to at least 191° C. The injector system has in fact been used at temperatures up to 255° C. FIG. 5 illustrates the injector assembly schematically. The sample was injected in sample inlet 302 through inlet check valve 304, after which it was transported through four-way connector 306 to trap/sample loop 308. At the proper time, the microprocessor controller set injector carrier valve 310, four-way connector 306, and three-way connector 314 to allow carrier gas from injector carrier source 312 to carry the sample from trap/sample loop 308 to flow restrictor 316. A heater (not shown) was used to volatilize sample components from trap/sample loop 308 as part of this operation. Column carrier valve 318 and electronic pressure control valve 320, along with four-way connector 306 and three-way connectors 314 and 324 were set to allow carrier gas from column carrier source 322 to carry a selected amount of the sample from flow restrictor 316 onto the head of chromatography column 326 in a narrow band.

More specifically, in the initial, standby condition, injector carrier valve 310 was closed, sample pump valve 330 was closed, purge vent valve 328 was closed, and column carrier valve 318 was open. The entire injector was pressurized to the pressure setpoint for the column carrier gas, under the control of electronic pressure control valve 320 and column carrier pressure sensor 321. To take a sample, sample pump valve was 330 opened, and very shortly afterwards sample pump 332 was started. When the pressure at 4-way connector 306 dropped to 0.33 psi below atmospheric pressure (an opening point determined by the "cracking pressure" of inlet check valve 304), inlet check valve 304 opened, and sample flowed through sample inlet 302 into the injector. At this point injector carrier valve 310 was closed, so that the only carrier gas into the injector could flow through column carrier valve 318. The volume of flow restrictor 316 was chosen to prevent excessive dilution of the sample because of too much carrier gas. The degree of flow restriction required depended on the length and diameter of the particular chromatographic column 326 being used with the injector. Longer, narrower chromatography columns required greater flow restriction. After the sample was taken, sample pump 332 was turned off, and sample pump valve 330 was closed. Before the injector was re-pressurized by column carrier flow, column carrier valve 318 was closed, and injector carrier valve 310 was opened. The resulting carrier flow through the injector backflushed the contents of sample loop 308 onto column 326. When the desired volume had flowed into column 326, column carrier valve 318 opened, purge vent valve 328 opened, injector carrier valve 310 closed, and any excess sample was vented as waste through purge vent valve 328. The precise relative timing of opening and closing these valves determined when (and whether) trap/sample loop 308, flow restrictor 316, or both were purged. The venting thus controlled the amount of sample injected onto the column, and also "cuts off the tail" of the sample injection plug, resulting in sharper peaks. The venting also cleaned the injector in preparation for the next sample.

Note that the sample contacted only deactivated fused-silica in the injector, except in the stainless steel (SS316) inlet check valve 304, where it contacted stainless steel and Viton™ inert fluoroelastomer. The check valve could be replaced with a inert glass-to-glass seal, a Teflon™ on-off valve, a septum, or other input device.

Such an injector/extractor has a number of advantages over prior injectors. Flow restrictor 316 optionally allows carrier gas to vent at all times, except when a sample is being drawn. This design allows the column flow to be maintained at a controlled rate at all times, thus preventing column back flow. This configuration dilutes the sample only while it is flowing to trap/sample loop 308; when the sample is back-flushed into the column, no dilution occurs, a distinct advantage over prior designs. The system design allows flexible purging of the system through a separate vent valve, rather than through the sample inlet. Venting through an adsorbent-filled tube as required by some prior designs generally is not desirable, although such venting may readily be accommodated where desired. The system can accept liquid samples through inlet 302, through the auxiliary liquid inlet described below. The system is not limited to cryofocusing applications, and can use other inlet (or sample processing) modules. Utility consumption is minimal.

Figure 5A:
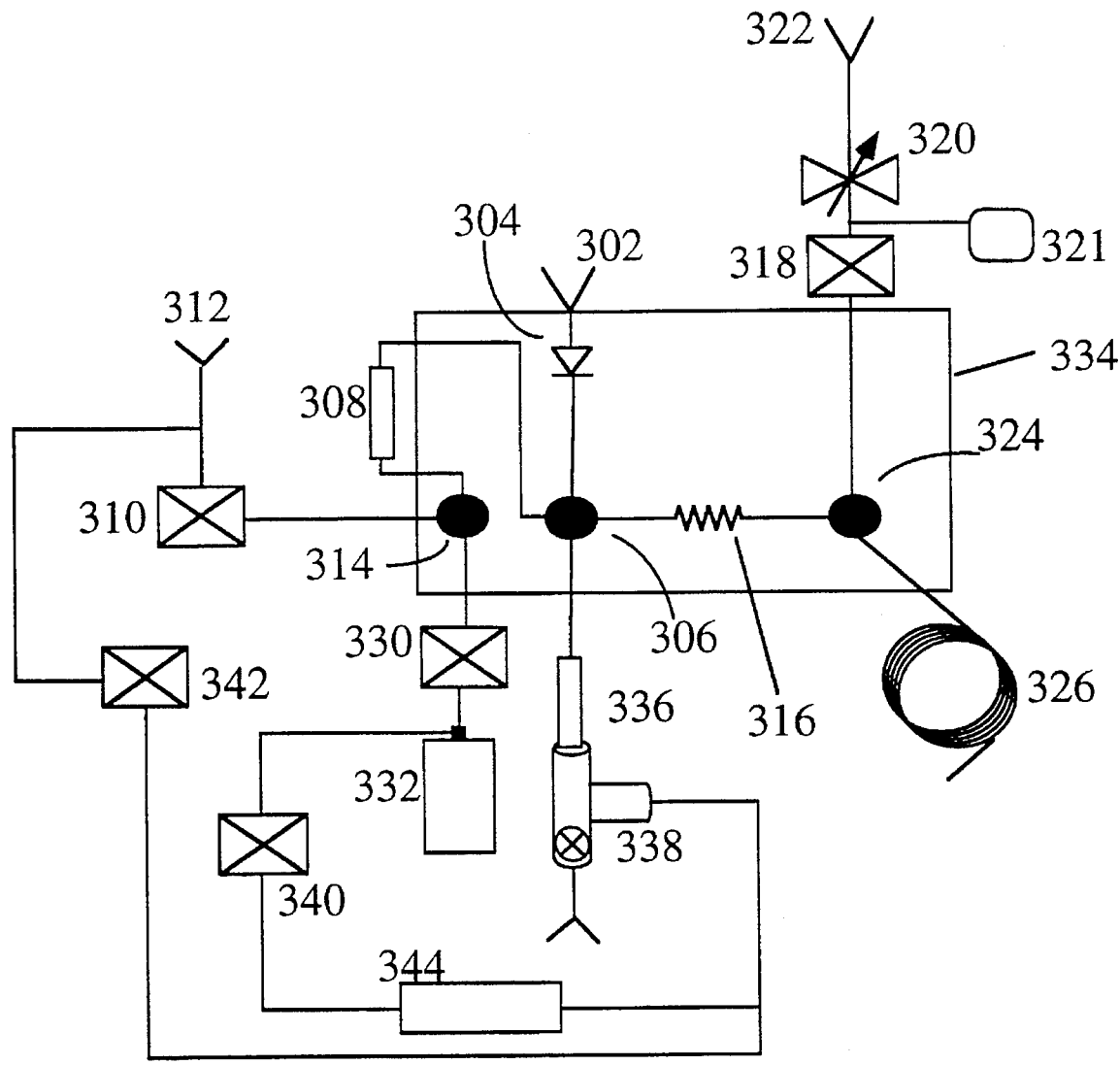
FIG. 5a illustrates schematically an injector assembly in a two-inlet configuration, with an automatic gas phase sample inlet and a liquid sample inlet.

An alternative means of injection is to inject a liquid sample at ambient temperature, and expose the liquid to vacuum to evaporate the solvent (or other relatively volatile components that are not necessarily solvent), followed by heating the sample. An injector suitable for liquid samples is illustrated in FIG. 5a. Except as otherwise indicated, numbered elements correspond to the same elements as illustrated in FIG. 5. A liquid sample was injected into cold sample loop 36 through inert (e.g., Teflon) syringe valve (or septum) and "T" connector 338. The liquid sample was literally placed directly into sample loop 336 with a syringe having a needle long enough to extend into the loop. After the sample was placed into the sample loop, vacuum pump 332 was actuated, and auxiliary vacuum valve 340 was opened. Note that injector carrier valve 310 and sample pump valve 330 remained closed during this step, isolating sorbent trap 308 from the gas flow paths used with the liquid injector. Sample loop 336 was large enough so that when sample pump 332 pulled carrier gas and/or air through sample loop 336, the liquid phase of the sample did not move out of sample loop 336 as a plug, but instead the solvent vapors above the liquid were swept out. In this manner, the volatile components were completely removed from the sample, and only semivolatile compounds having low vapor pressures remained. (How low the vapor pressures of the non-evaporated compounds was depended on how long the sweep continued; as in a distillation, the early stages of the sweep removed primarily volatile components, while later stages continuously removed less volatile constituents). When the solvent was sufficiently removed, vacuum pump 332 was turned off, and sample loop 336 was heated to an elevated temperature (e.g., 200° C.) with no flow to the system yet. (With no flow to the system, rapid heating of sample loop 336 became less important, reducing power demand.) After sample loop 336 was heated to the selected temperature, carrier gas valve 342 was opened to allow carrier gas to flow through sample loop 336, through four-way connector 306, and then onto column 326. Because the compounds present had low vapor pressures, they tended to accumulate in a narrow band at the head of column 326 when the temperature there was held low (e.g., room temperature), and were not yet carried into the column. Large volume, replaceable guard trap 344 acted to protect downstream components from contaminants.

(Note that the volatilities of compounds that accumulated at the column head and those that did not was a continuum. There was no sharp, abrupt change between compounds that did not accumulate and those that did. Even so, the differential between compounds that tend to accumulate at the column head at a given temperature and those that did not is often a useful tool in performing separations.)

Arialumina-silica housing (not shown) was used to house the injector. The housing provided sufficient thermal insulation to keep the external surface temperature below 50° C. when the injector was heated to 220° C. A thermally conducting sheath around the sample inlet kept the temperature of the sample inlet port above 50° C. The sample inlet itself was not strictly within the controlled temperature zone, but it did reach a steady-state temperature between the temperature of the injector and the ambient air temperature.

The sample inlet 302 was made from stainless steel. A sequence of pneumatic valve operations controlled by the on-board microprocessor directed the flow of the sample through the sample inlet 302, through the other injector components as previously discussed, and then onto the column. The valve sequence was specified from an external computer or terminal via serial communications, using the commands shown in Table 1 (see "Control Electronics" section below). Optional adsorbent trap 308 could be thermally desorbed at any time during the sequence, as specified by the user. The trap may be open, wall-coated, or sorbent-filled. Multiple traps or columns may be used in the GC, connected via pneumatic valves. Different traps or columns may then be specified by the user, with the microprocessor routing samples to the desired trap or column in place; no equipment need be changed in the field. By appropriate switching of valves, a backflow of gas from inlet 322 can be used to clean a column, injector, etc. Greater efficiency may result from cleaning one portion of the system (e.g., retention gap 316, and optionally trap 308 as well) while another portion (e.g., column 326) is in use.

The injector used a regulated carrier gas supply at inlet 322 at a pressure between 40 and 80 psi. The gas was supplied through an external, manually controlled regulator. An electronic pressure regulator 320 further reduced the pressure to provide the desired carrier gas flow rate. The carrier gas flow rate was controlled through commands to the controller board from an external terminal. The carrier gas is preferably hydrogen or helium. In the field, an $H_2$ carrier gas could be generated easily and inexpensively by electrolysis of water, with the electrolysis occurring either internal or external to the rest of the unit.

The basic design of the novel chromatograph allows a wide variety of specific instrument configurations, to fit particular intended uses. For example, one version of the chromatograph might have one injector/extractor in the SPM and two different columns in the AM, tailored to fit a specific application. Another version might have two different sample injector/extractors in the SPM, and one column with two different detectors in the AM tailored to fit another application. Another version, intended to be useful in a variety of applications, might have three different injector/extractors in the SPM; and two different columns, each with two detectors in its AM. The software used with the chromatograph can also be tailored to serve a particular application, if desired. See, e.g., FIG. 2(a), illustrating an embodiment of this invention having a single injector and a single column; and FIG. 2(b), illustrating an embodiment having multiple injectors and multiple columns.

Figure 1:
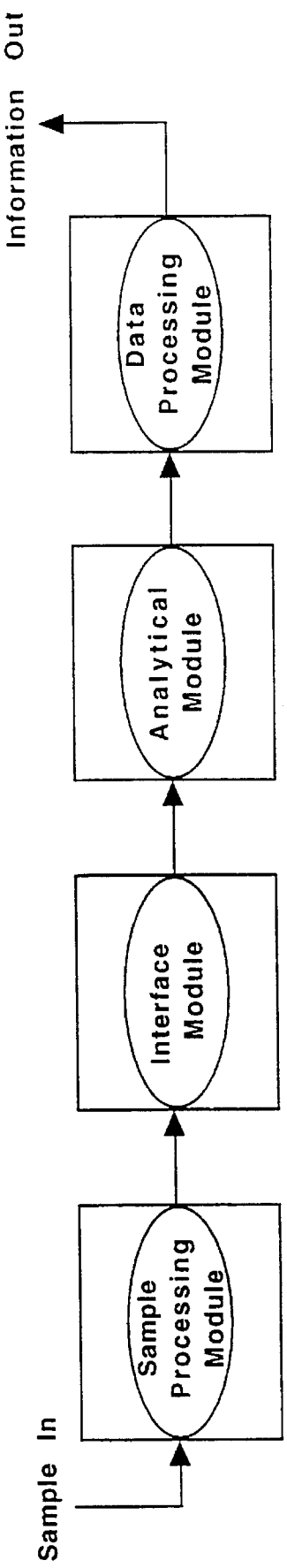
FIG. 1 illustrates one embodiment of the present invention schematically, showing components of the Sample Processing Module (an isothermal or temperature programmable, heated inlet/extractor-injector), the Interface Module, and the Analyzer Module (analytical column and oven with detector).
Figure 2A:
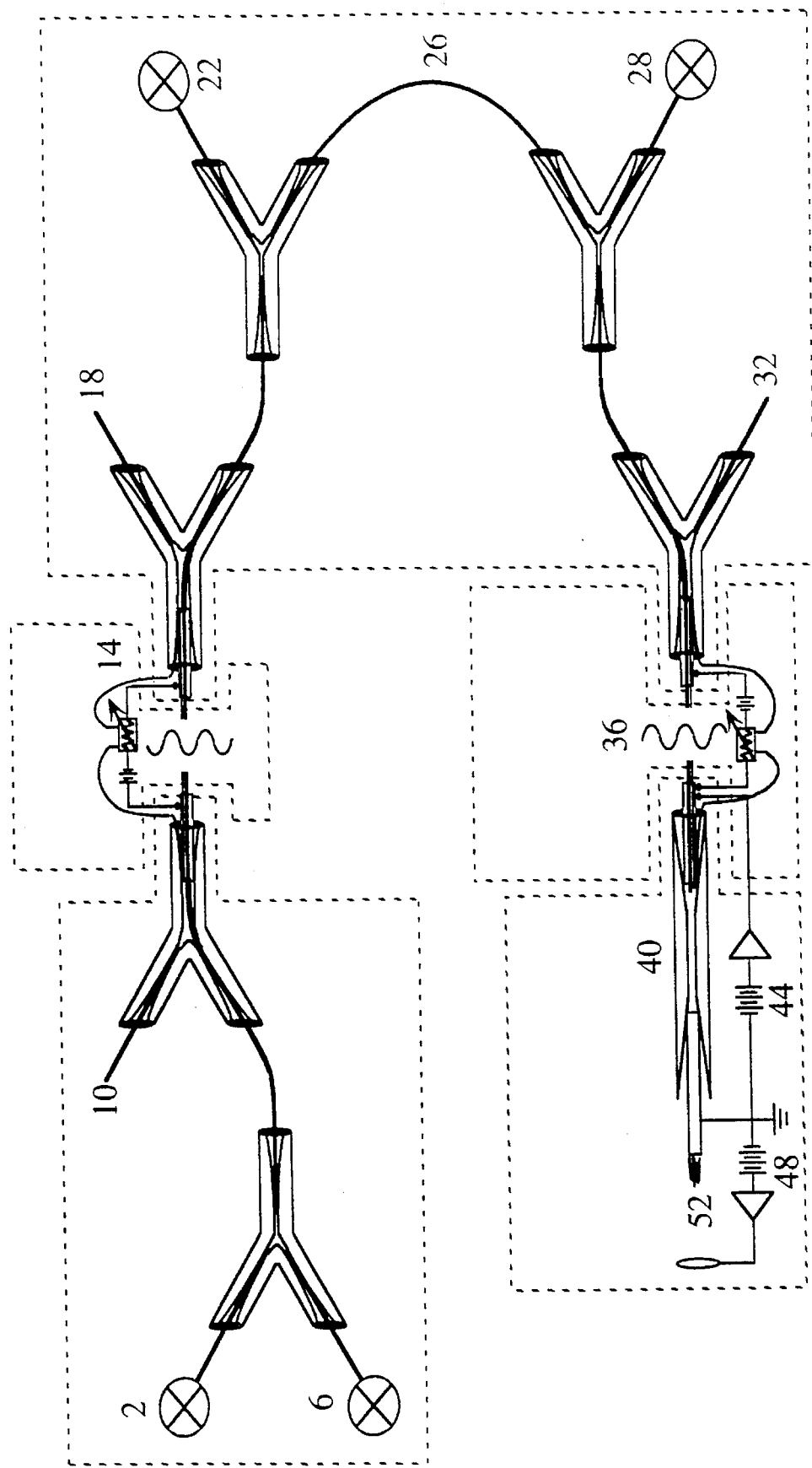
FIG. 2(a) illustrates an embodiment of this invention with a single extractor-injector and a single analytical column.
Figure 2B:
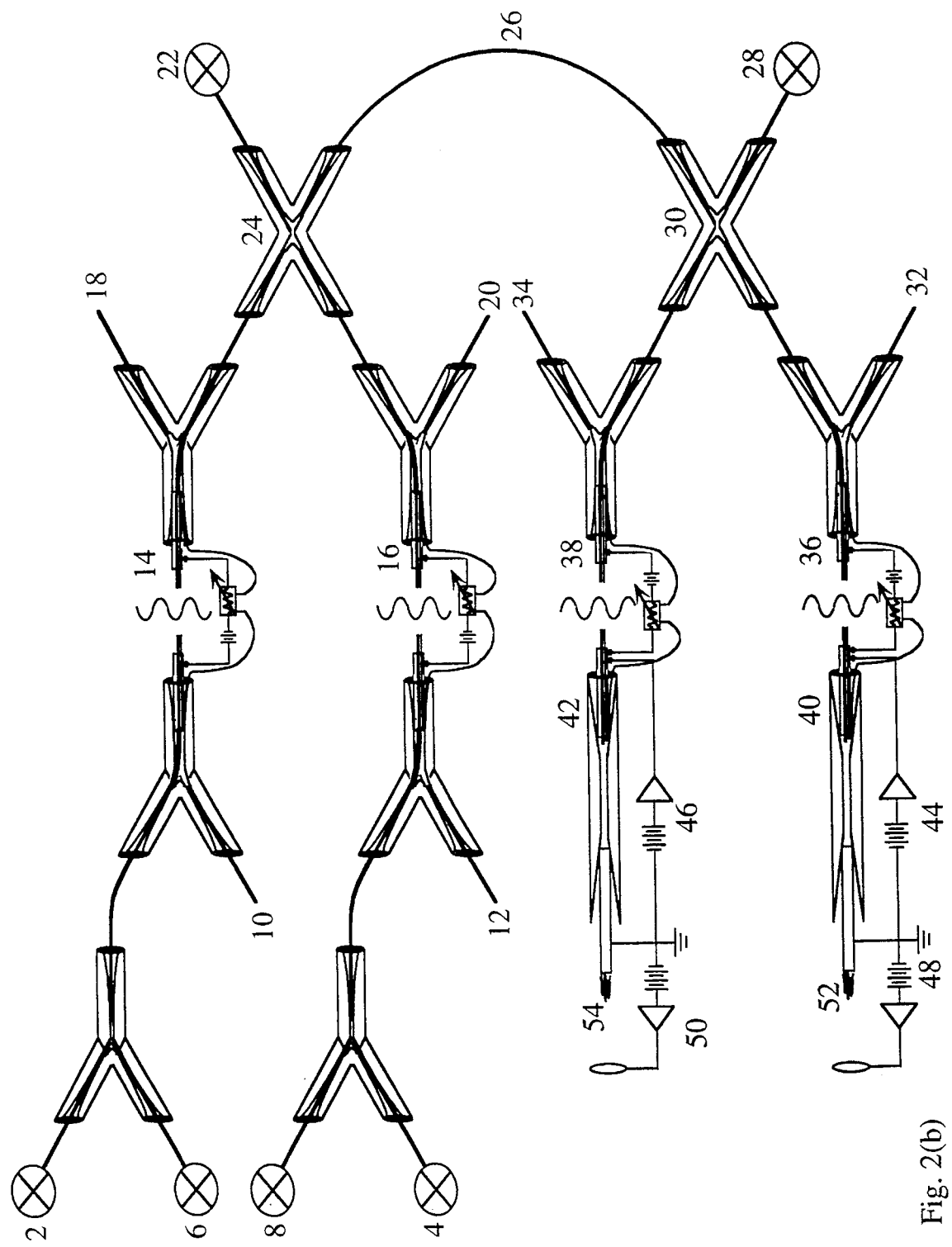
FIG. 2(b) illustrates another embodiment of the present invention schematically, showing the Sample Processing Module with two open, tubular-type extractor-injectors, the Interface Module, and the Analytical Module with two column/oven/detector combinations.

Referring to FIGS. 2(a) and 2(b), a carrier gas such as hydrogen or helium is admitted through valve 2 or 4. The sample is injected through valve 6 or 8. A sheath gas for homogenizing heat distribution is admitted through inlet 10 or 12, and exits through outlet 18 or 20. Pump 22 draws the sample through the sample inlet, valve 6 or 8, into a temporary holding tube or trap 14 or 16, where the sample remains until it is heated. The carrier gas admitted through valve 2 then carries the sample to retention gap column 26, and then onto column 36 or 38. Carrier gas 28 then drives the carrier gas through column 36 or 38, and can also backflush retention gap 26, and optionally tube 14 or 16, while the sample is running in the column. This approach saves time, which is particularly important when multiple samples are to be analyzed. (Carrier gas 28 is preferably able to reach full operating pressure in less than about 20 msec.) Quartz connector 40 or 42 connects the output of column 36 or 38 to the detector or detectors. As depicted here, there are two detectors, a photoionization detector 44 or 46; and a flame ionization detector 48 or 50, with hydrogen flame 52 or 54.

Figure 3:
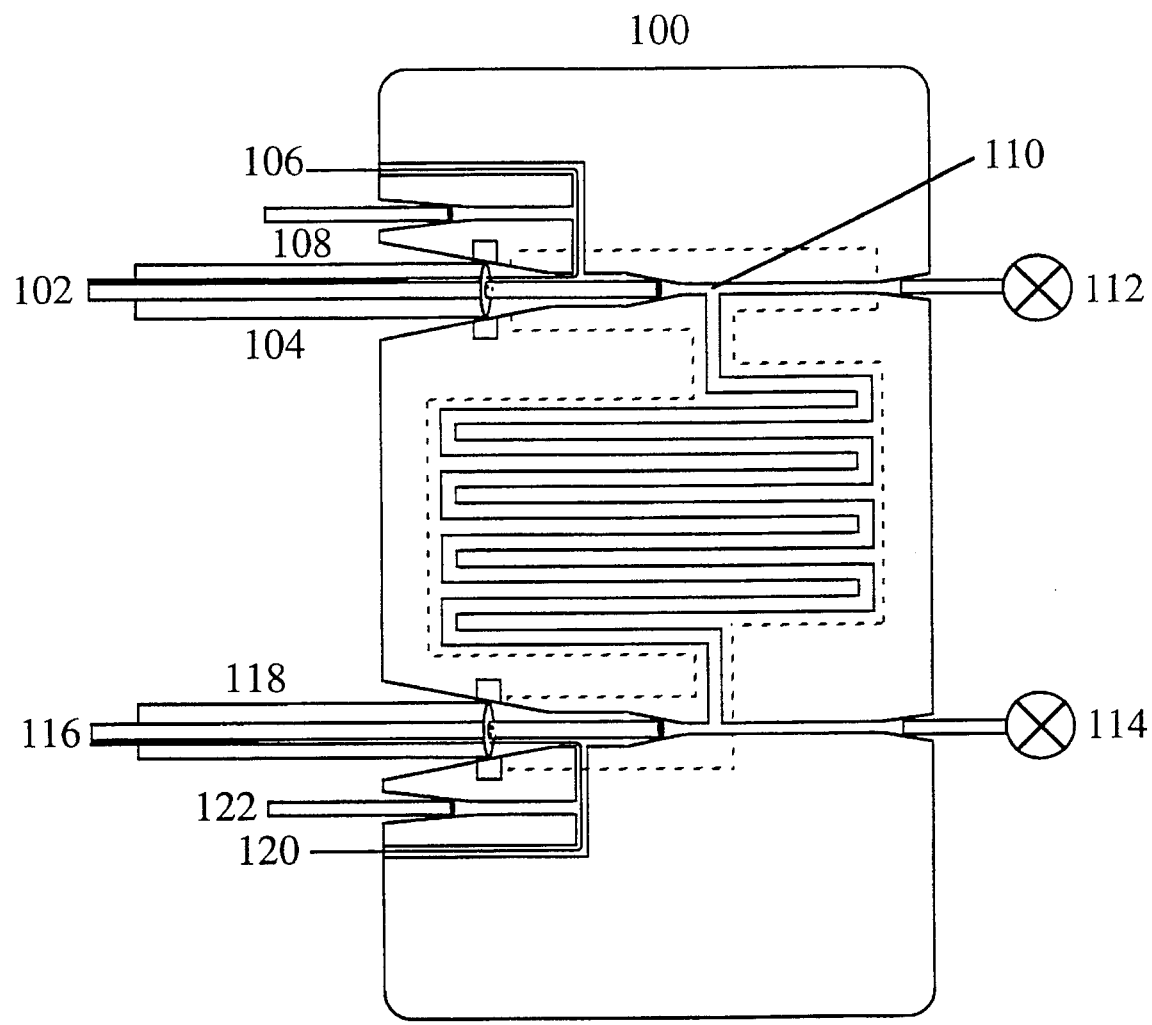
FIG. 3 illustrates one embodiment of the Interface Module, with a heated zone retention, gag-type connection between a single extractor-injector and a single analytical column-oven combination, fabricated via micromachining technology to include electrical and pneumatic connections and low thermal mass heaters.

In a preferred embodiment, a portion of the injector/extractor will be micromachined in silicon through known micromachining technologies. As illustrated, for example, in FIG. 3, injector column 102 fits into micromachined chip 100. Temperature sensor wire 106, which runs parallel to the injector column, exits the chip to lead to appropriate circuitry. Heater tube 104 surrounds injector column 102. Sheath gas from heater tube 104 exits chip 100 through outlet tube 108. Retention gap 110 functions as previously described, and is surrounded by an electrically resistive heated zone (not shown) in chip 100. Carrier gas from valve 114 and pump 112 act to send a selected amount of sample into analytical column 116, and to backflush retention gap 110, as otherwise previously described. Temperature sensor wire 120, which runs parallel to the analytical column, enters the chip from appropriate circuitry. Heater tube 118 surrounds analytical column 116. Sheath gas to flow through heater tube 118 enters chip 100 through inlet tube 122.

The Column

Figure 6:
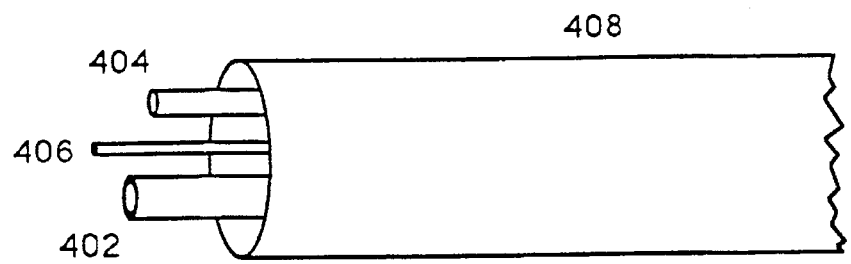
FIG. 6 illustrates the column assembly schematically.

A low-thermal-mass column allowed fast, temperature-programmed chromatograms, and relatively short turn-around times (about 2 minutes) in analyzing semivolatile analytes (those having retention indices up to about 2000). The column assembly, illustrated in FIG. 6, comprised a 3 meter×100 micron inner diameter (i.d.) column 402, a resistive heater 404, and a temperature sensor 406, all housed in a 1.1 mm i.d. polytetrafluoroethylene (PTFE) tube 408. The inner diameter of the column is preferably less than about 270 microns.

The electrical-resistive heater 404 used was a 0.5 mm diameter Constantan™ nickel-copper alloy wire having an electrical resistivity of 120 Ω-cm. Preferably, the heater could instead be a tubular heater made from a Monel 400™ copper-nickel alloy tube, in which the tube diameter is selected to provide the desired total resistance for a given length of column. By placing the column in a tube, and supplying heat directly from the tube, more even heating results than can be obtained, for example, by heating an aluminum-clad fused silica column in which the aluminum acts as a resistive heater. The clad column is more susceptible to hot and cold spots, and is also quite susceptible to breaking due to different thermal coefficients of expansion.

The column had a very low thermal mass. It also had very good temperature stability because of the rapid control feedback. The column, when coiled into a small helix, occupied a space less than 60 cm³. An enclosure (not shown), made from the same material as was used for the injector housing, held the column within the chromatograph. This enclosure reduced power consumption during temperature programming by reducing the heat lost from the column assembly. The column/heater assembly extended into the adjacent heated zones (injector and detector) to minimize the cold spots that might otherwise occur if the column passed through unheated regions. A fan mounted on one end of the column housing was used to cool the column assembly after completion of a temperature-programmed run. For example, after a temperature-programmed run to 230° C., the fan cooled the column to 40° C. in less than 90 seconds. The rapid cooling is possible due to the low thermal mass of the column/heater/sensor combination. Alternatively, a small, low power air pump capable of pumping 2 to 4 liters of air per minute through the void space of the column housing could be used with a greatly reduced void volume to provide higher cooling rates.

The upper limit on the heating rate depends primarily on the power available from the heater power supply. The breadboard embodiment had a heater resistance of 2 ohms, and could supply over 200 W to the column heaters with a 24 V power supply rated at 10 A. A similarly rated 18 V power supply would supply approximately 125 W. The column and housing design described above required approximately 110 W to maintain a temperature program rate of 5° C./sec at 230° C. At a rate of 1° C./sec the power requirement dropped to 65 W at 230° C. Isothermal temperature control required 7 W at 50° C. and 24 W at 240° C. Temperature stability was observed to be superior to that of a more conventional gas chromatography oven, even if the latter is held under isothermal conditions. Furthermore, while a conventional GC oven could not control the column temperature at programming rates much higher than about 1° C./sec, the working prototype of this invention described above could control the temperature ramps at rates up to 10° C./sec.

Note that for optimal response, most of the length of the elongated or coiled column, preferably at least 80% of the length of the column, should be positioned substantially parallel to the coiled or elongated heater. (The term "substantially parallel" should not be interpreted in a geometrically precise way; rather, the term means that the paths of the column and heater are in close proximity, and that the two paths run more-or-less in tandem.) It is preferred that most of the length of the column, preferably at least 80% of the length of the column, should be within 5 mm of the nearest point of the heater.

The column may be placed substantially inside a tube, where the heater is the tube itself, or where the heater is also contained substantially within said tube. The heater should not be an electrically resistive film that adheres to the outside surface of the column over substantially the entire length of said column, because such an arrangement typically has problems with breakage due to uneven thermal expansion. Alternatively, a thin metal film could be deposited on the interior of a quartz tube. The thin inner film may be more flexible, and thus not break the tube. Instead, on heating the film might distort—which might be a problem if it were in the column, but not for the heater, because the heating film is not attached to the column. The temperature sensor may also be the tube itself, or it may also be contained substantially within the tube. The same electrically resistive element may be used on the one hand as a heater, and on the other hand as a resistive temperature sensor.

Alternatively, the column, heater, and temperature sensor may lie on or within a thermally insulating material on the surface of a cylindrical support. For example, they can lie within spiral grooves on the surface of the insulator.

The Detector

For expediency in testing, the detector which has been used in the prototype embodiment to date was one from a conventional bench-top gas chromatograph. In the future, preferred embodiments of the invention will use detectors made on as small a scale as is the rest of the chromatograph. A currently available small-scale detector is a micro thermal conductivity detector manufactured by MTI Analytical Instruments (Fremont, Calif.). Suitable detectors should be miniaturized to be compatible with the small volumes and low resource consumption of the novel chromatographs.

Suitable detectors should work well with the small sample sizes, fast response times, and low utility consumptions that are characteristic of the portable chromatographs of this invention. Miniaturization of the detectors will allow the use of multiple detector options, without unacceptable sacrifices in size or portability. Among the detectors that should be useful in practicing this invention are the following: flame ionization (FID), photoionization (PID), helium ionization (HID), argon ionization (AID), RF-coupled helium ionization, micro-thermal conductivity (µTCD), direct field ionization, flame photometric (FPD), pulsed flame photometric (PFPD) and photoinduced photoemission. Of these options, the FID, PID, HID, AID, µTCD, and FPD are established GC detectors available B commercially from such companies as Hewlett-Packard (Palo Alto, Calif.), SRI Instruments, OI Analytical (College Station, Tex.).

A prototype miniaturized FID has been built and tested. This prototype operated successfully on only 5 ml/min of hydrogen and 50 ml/min of air. Other detectors believed to have particular promise for miniaturized applications include helium ionization, field ionization (both direct and RF-coupled), and multi-wavelength photoemission detectors.

Figure 4:
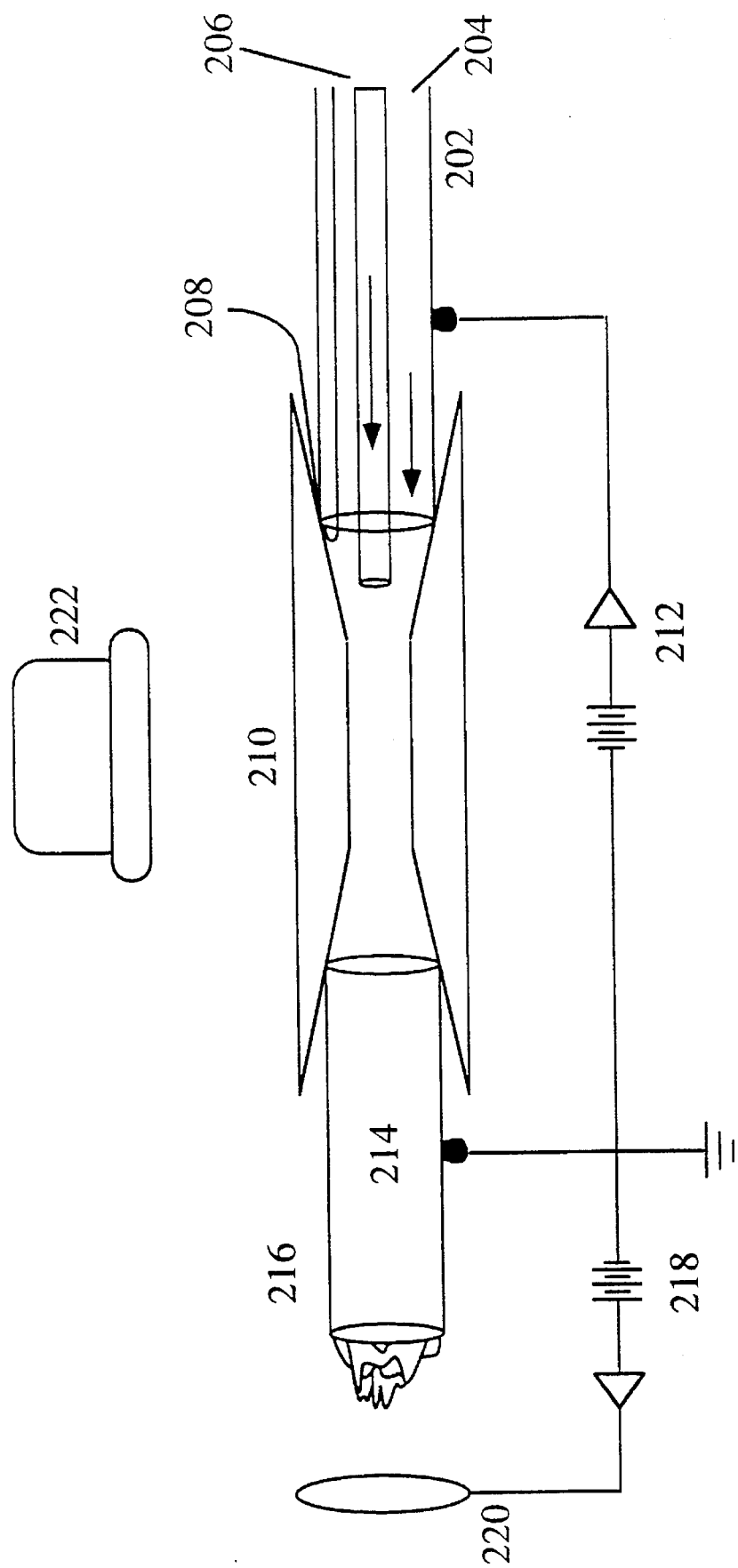
FIG. 4 illustrates one embodiment of a low thermal mass tandem PID/FID detector combination designed to conserve consumption both of compressed gases (e.g., hydrogen carrier gas) and of power.

FIG. 4 illustrates one embodiment of a low thermal mass tandem PID/FID detector combination designed to conserve consumption both of compressed gases (e.g., hydrogen carrier gas) and of power. As illustrated in FIG. 4, tubular heater 202 surrounds a heated sheath gas 204, the outlet 206 from an analytical column, and temperature sensor wire 208. The gases flow through transparent quartz connector 210, where ultraviolet light source 222 sends light through the flowing gas, causing changes in conductivity that may be detected with photoionization detector 212. (Note the electrical connections between detector 212, tubular heater 202, and tube 214.) After exiting the photoionization detector, the sample immediately enters stainless steel tubing 214, with hydrogen flame 216 activating flame ionization detector 218 and FID collector electrode 220.

The use of two detectors in this manner permits efficient use of time in performing the analysis, and increases the confidence of sample identification when two different detection means are used more-or-less simultaneously.

The Sorbent Trap

The injector system had an optional heated sorbent trap operated by the control board to "preconcentrate" samples. The heater was a tubular resistive heater that would accept 1.6 mm o.d. tubing. The heating element resistance was 17 Ω. The sensor wire had a nominal resistance at room temperature (25° C.) of 20 Ω with a thermal coefficient of resistance of 4500 ppm/°C. As with the other controlled parameters, the timing and temperature setpoints for the thermal desorption could be uploaded from a remote computer terminal.

The trap itself comprised approximately 5 mg of 60/80 mesh Tenax-GC™ p-phenylene oxide polymer packed in a 0.7 mm i.d.×1.6 mm glass-lined stainless steel tube. Other sorbents commonly used in gas chromatography could also be used. Nickel tubing silver-soldered to the trap ends connected the trap to the injector system. The trap heater was long enough that the nickel tubing through which the sample passed could be heated along with the trap.

Alternatively, an open tubular trap may be used that is similar in construction to the packed trap, except that an inert Teflon valve will be used for injection of sample extracts in volatile organic solvents directly into the open tube. While at ambient temperature, the solvent will be evaporated under a gentle flow of carrier gas. The trap will then be heated to 250° C., and the carrier gas flow directed onto the head of one or more ambient temperature analytical columns. The analytes will thus be evaporated and injected in a narrow band onto the analytical columns for chromatographic analysis. After the injection, the open tubular trap will be purged with carrier gas and cleaned for the next sample injection.

The Control Electronics

A controller board (not shown) was used to control all time and temperature setpoint values for the valves, injector, column, and detector. The controller board also controlled column gas flow via an electronic pressure control system using a Redwood Microsystems Fluistor™ control valve. In the breadboard prototype embodiment, the various parameters were uploaded from an external terminal using the command set shown in Table I.

TABLE I

GC CONTROLLER COMMANDS

| | |
|---|---|
| T1 | Sets the initial column temperature in °C. |
| T2 | Sets the final column temperature in °C. |
| T3 | Sets the injector temperature in °C. |
| T4 | Sets the detector temperature in °C. |
| T5 | Sets the trap temperature in °C. |
| D1 | Sets the initial ramp delay in seconds for heating the column. |
| D2 | Sets the final ramp delay in seconds. |
| D3 | Sets the cycle time in seconds. |
| Vn | Sets the valve n (n = 1 . . . 6) start time in 10 ms units. |
| Kn | Sets the valve n (n = 1 . . . 6) stop time in 10 ms units. |
| X | Reopens the sample valve to vent excess sample from the injector |
| H1 | Sets the trap heater start time in 10 ms units. |
| H2 | Sets the trap heater stop time in 10 ms units. |
| C1+/− | Enables/Disables the column temperature control. |
| C2+/− | Enables/Disables the detector temperature control. |
| C3+/− | Enables/Disables the injector temperature control. |
| C4+/− | Enables/Disables the trap temperature control. |
| F+/− | Enables/Disables the column head pressure controller. |
| R+ | Starts the ramp. When the final temperature is reached, the temperature is maintained at the final temperature. |
| R− | Disables the ramp. The temperature is allowed to return to the initial temperature. |
| Z1 | Calibration factor for column temperature sensor. |
| Z2 | Calibration factor for trap/sample loop temperature sensor. |
| P | Sets the column head pressure setpoint in PSI. The pressure is entered as 10 × pressure. |
| S | Sets the rate of the column temperature heating ramp in °C./second. The number is entered as 10 × rate. |
| G | Starts the sequence. |
| A | Displays the current pressure in PSI. |
| B | Displays the current injection valve sequences, temperature control sequences, and pressure control settings. |
| <CTRL> C | Resets the controller. |

The system used resistance temperature detection (RTD) to measure both column and trap temperatures. The resistance of the wire changes according to the formula $R_T = R_0(1+\beta T)$, where T is the temperature in degrees Centigrade, $R_T$ is the resistance at temperature T, $R_0$ is the resistance at 0° C., and $\beta$ is the temperature coefficient of resistance. A constant 10 mA current passing through the sensor generated a voltage linearly dependent on the temperature. Detector and injector temperatures were sensed by type-K thermocouples. In future embodiments of the invention, it is expected that the thermocouples will be replaced with RTD's as well. The use of RTD's in all zones will allow better estimates of average temperatures, will simplify the controller, and will reduce construction costs. The controller continuously compared the set point temperatures with the measured temperatures, and appropriately adjusted the power delivered to the various heaters by pulse-width modulation of the heater voltage.

The carrier gas pressure was controlled by an electronic pressure regulator using a Redwood Fluistor™ flow control valve, using a proportional integral and derivative (PID) algorithm. The PID control algorithm was executed 4 times per second, and the output of this computation was applied to the regulator to control the pressure.

An internal timer generated interrupt signals every 10 ms. The 10 ms interrupt signals were used as the basic timing unit for the system.

Setup methods could be sent to the unit from a dumb terminal emulator, or uploaded from an external computer. Table II shows a typical set of commands used to prepare the unit for a 10 second sample time and a 205 ms injection, with no preconcentration. The sample run would then be started by sending a "G" command to the controller.

TABLE II

Typical command sequence for 10 second sample time with 250 ms injection

| | |
|---|---|
| V1 | 1 |
| K1 | 1000 |
| V2 | 1 |
| K2 | 1000 |
| H1 | 65,500 |
| H2 | 65,500 |
| V3 | 1002 |
| K3 | 1027 |
| V4 | 1000 |
| K4 | 5002 |
| V5 | 1027 |
| K5 | 5002 |
| X | 65534 |
| D1 | 0 |
| D3 | 240 |
| Z1 | 2484 |
| Z2 | 189 |
| T1 | 50 |
| T2 | 40 |
| S | 0 |
| T3 | 150 |
| T5 | 200 |
| P | 250 |
| F+ | |
| C1+ | |
| C3+ | |

In Table II above, V1, or valve 1, denotes sample pump valve 330 of FIG. 5; V2 denotes sample pump 332; V3 denotes injector carrier valve 310; V4 denotes column carrier valve 318; and V5 denotes purge vent valve 328.

Operation

The power connections on the breadboard embodiment described above had a wire-wrapped control board, and required two separate external power supplies, a ±15 V DC supply for the control board and a +24 V DC power supply for the heating elements. On a printed circuit control board embodiment to be made, only a +24 V supply will be required; a ±15 V power supply can then be provided on the circuit board itself. Power supplies, solenoid valves, heaters, and temperature sensors all attached to the circuit board.

When the controller received a start signal (ASCII character "G") from an external source (such as a computer), the controller began a valve and temperature control sequence determined by the parameters previously uploaded from the computer. Between injection sequences, the controller maintained a constant temperature in all heated zones, and also maintained the column head pressure. The set points for these "idle" conditions may also be set from the external computer.

Injector Performance

The injector allowed the use of either liquid or gaseous samples. The injector system could refocus semivolatile compounds from a sample into a narrow plug at the column head before introduction onto the column. The chromatograph design allowed samples to be injected either from an injection loop or from a sorbent tube concentrator.

Figure 7:
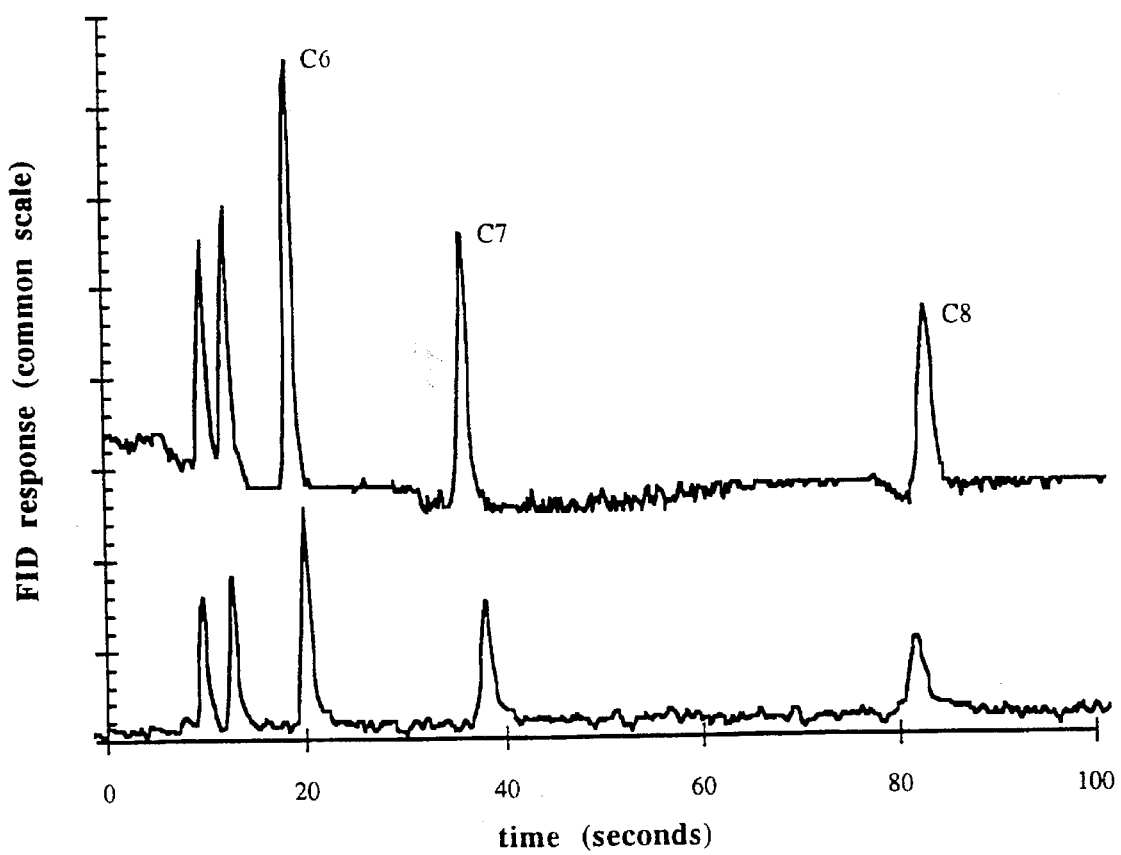
FIG. 7 illustrates separations achieved for a mixture of volatile organic compounds, the n-alkanes butane through octane.

The results are illustrated in FIG. 7, which shows that the injector was capable of delivering samples to the column at least as effectively as a current, commercially available microchip injector. FIG. 7 shows the separations achieved for a mixture of n-alkanes (butane through octane), each at a concentration of 100 ppm by volume. The top graph depicts the results obtained with the novel injector, while the bottom graph depicts results obtained with the commercially available injector.

Column Performance

Figure 8:
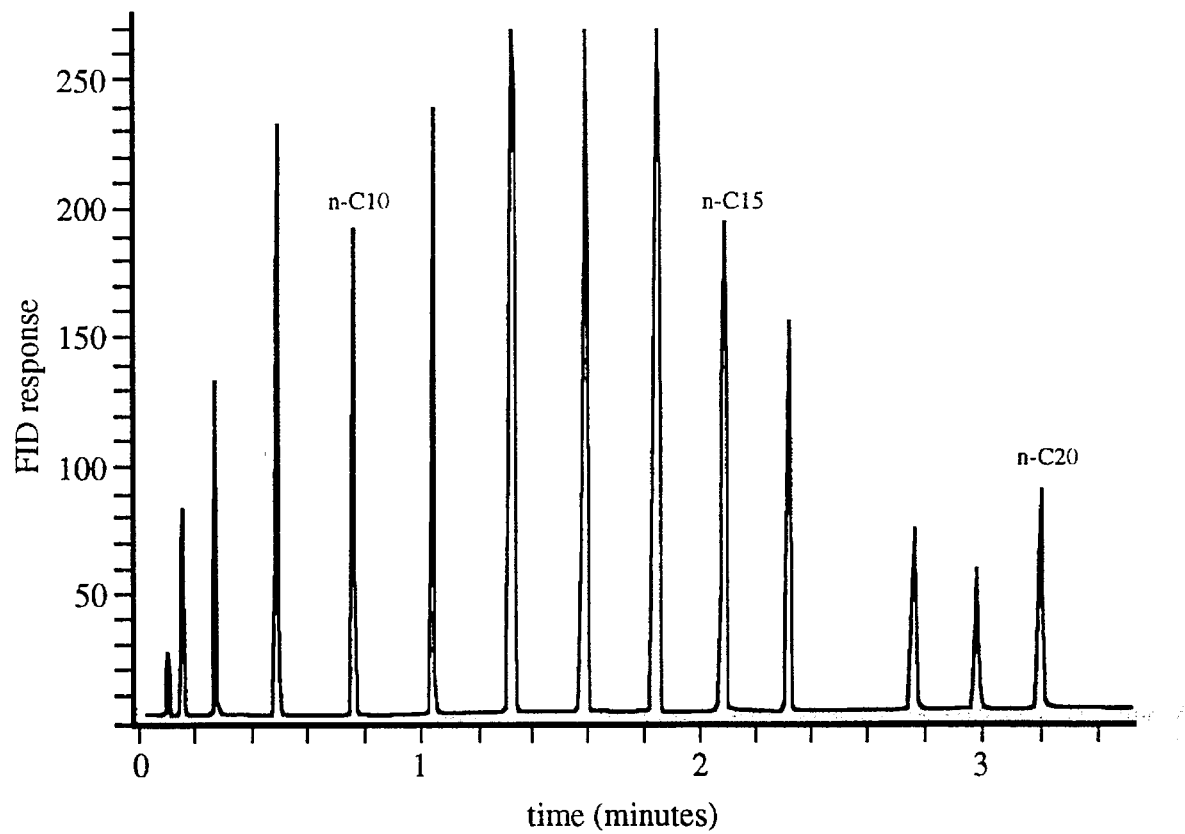
FIG. 8 illustrates a chromatogram of a distillation standard containing various semi-volatile organic compounds, various alkanes up to n-$C_{44}$, dissolved in carbon disulfide.

The column was capable of maintaining temperatures above 200° C., and of handling temperature programming rates up to 10° C./sec. The column readily analyzed alkane standards having retention indices up to 2000. FIG. 8 illustrates a chromatogram of a distillation standard containing various alkanes up to n-$C_{44}$, dissolved in carbon disulfide. One microliter of headspace vapor from this sample was introduced onto the column by splitless injection from the injector of a Hewlett-Packard HP5890 chromatograph. The column and heater provided excellent chromatography for compounds from n-hexane to n-eicosane. Eluting peaks for higher boiling components (those above about $C_{20}$) (not shown) were increasingly distorted, an effect believed to be due to cold spots between the column and the detector. (These cold spots are believed to be an artifact of the manner of construction of the prototype embodiment described here, in which for expediency of testing the detector used was from a conventional bench-top gas chromatograph. The relatively long transfer line between the column housing and the detector could be heated or insulated to eliminate these cold spots. But in a preferred embodiment, the column will attach directly to a detector immediately adjacent to the column housing, a transfer line will not be needed, and these artifactual cold spots will no longer be present.)

Figure 9:
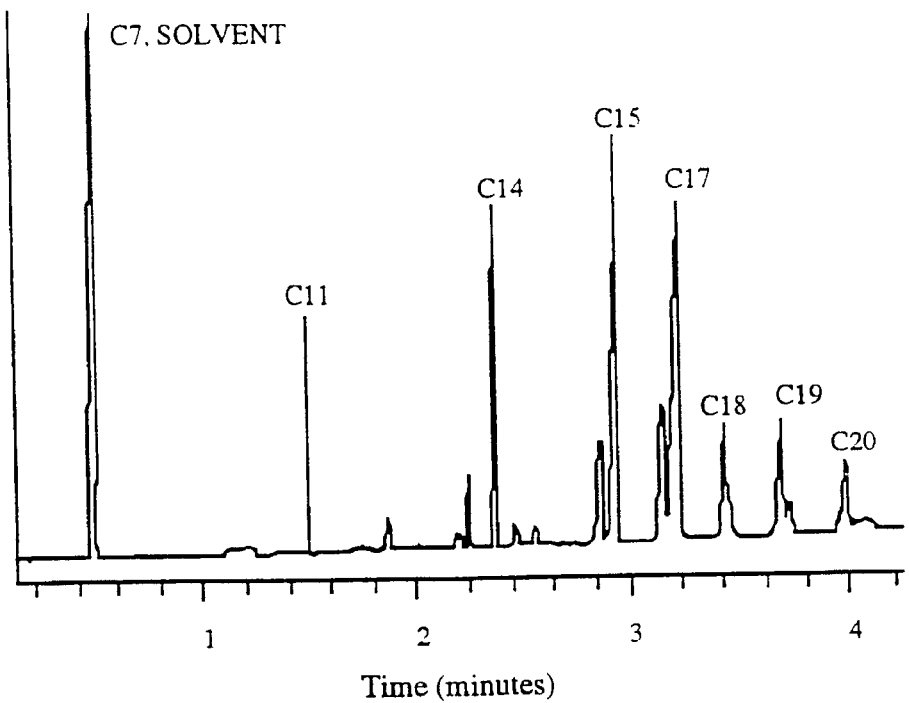
FIG. 9 illustrates a chromatogram obtained for 1 µL of a liquid heptane sample containing n-alkanes from undecane through eicosane.
Figure 10:
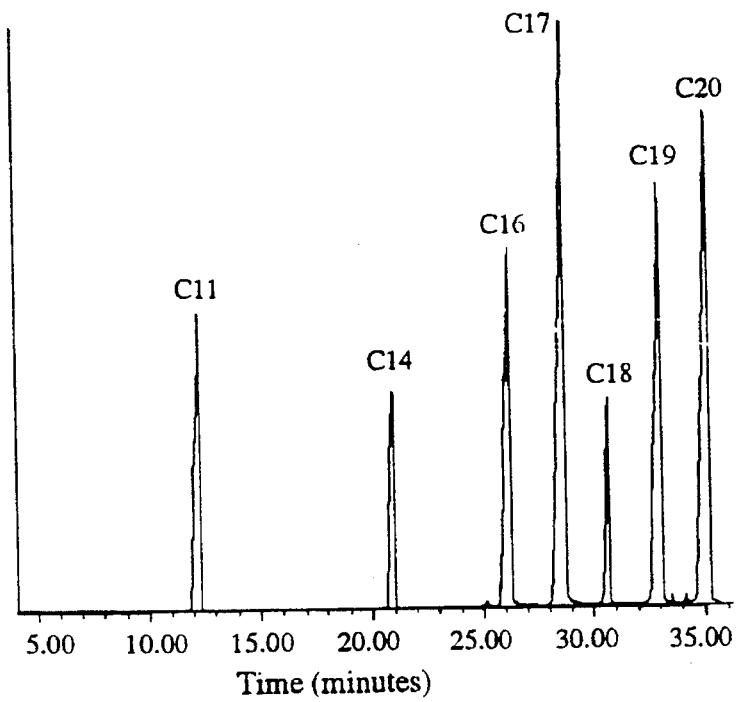
FIG. 10 illustrates the same sample analyzed with a commercially available, laboratory-based gas chromatograph.

FIG. 9 illustrates a chromatogram obtained for 1 µL of a liquid heptane sample containing n-alkanes from undecane through eicosane. FIG. 10 illustrates the same sample analyzed with a commercially available Hewlett Packard HP5890/5891 GC/MSD. Comparison of the two chromatograms indicates some discrimination for compounds having retention indices above 1700, i.e., octadecane and alkanes with higher molecular weights.

The results obtained in these tests did not even use the refocusing potential that is available for high-boiling compounds. Experiments with other systems have indicated that these columns can easily refocus analytes with retention indices above 900. Thus large volume samples can be concentrated at the head of the column, before the sample moves onto the column.

The reproducibility of temperature-programmed chromatographic retention times was better than 0.5% for compounds having retention indices above 900. Relative variability in retention times increased for more volatile analytes. The repeatability of these elution times compared well to the values of approximately 0.1% obtained for volatile compounds with a commercially available, MTI M200 gas chromatograph. Two possible reasons for the lower degree of reproducibility are less precise control of temperature at low isothermal column temperatures, and flow variability having a larger effect on poorly retained compounds.

The results obtained with the prototype embodiment described above are very promising. The injector and column perform competitively with current, commercially available portable instrumentation, and outperform any commercially available unit having such low power requirements.

Operating Parameters

Following are some of the more significant operating parameters and characteristics for the breadboard embodiment of the novel gas chromatograph:

Operating Environment

Operating Temperature Range 0° C. to 45° C.

Storage Temperature Range −20° C. to 60° C.

Relative Humidity Range 0 to 100% (non condensing)

Power Requirements 100 watts peak power 12 V DC supplied to the unit from power pack or other DC source; the power pack supplied 140 watt-hrs. uninterrupted power supply at 12 V DC.

Carrier Gas Supply 60 to 80 PSIG, 99.995% pure He or $H_2$, at flow rates up to 25 ml/min.

Sample Requirements

Air or gaseous samples at 0 to 30 PSIG at ambient temperature;

water or soil gas may be used for volatile organic compound ("VOC") analysis;

analytes may be introduced in organic solvents (dichloromethane, hexane, methylethyl ketone, toluene, methanol, etc.).

Dimensions

12" wide by 12" deep by 3" high (without associated laptop computer);

10 lbs. weight;

uninterrupted power supply external to the unit.

Standard Equipment

One or two independently controlled capillary columns, 3 m or 6 m long, each 0.1 mm ID;

temperature programmable from 0.1° to 5° C. per second, from ambient temperature to 250° C.;

two injectors, one open tubular and one packed with tenax/spherocarb adsorbents (0.7 mm ID, glass lined, 4 cm long);

one gaseous heated inlet through a check valve with vacuum pump sample introduction;

one liquid inlet for syringe injection of extracts in volatile organic solvents into ambient temperature open tubular injector.

Dynamic Range of Analytes

Volatile Organic Compounds (VOC's): RI 300 to 1000 (i.e., compounds with ambient temperature vapor pressures from 1 mm to 8000 mm of Hg).

Semivolatile Organic Compounds (SVOC's): RI from 900 to 3000 (i.e., compounds having vapor pressures from $10^{-9}$ to 3 mm of mercury).

Peak capacity of at least about 100, preferably at least about 500 for compounds having RI's in the range 300 to 3000, i.e., those having elution times between those of propane and n—$CH_3$ $(CH_2)_{28}CH_3$.

Deteactor Options

Micro Thermal Conductivity Detector (µTCD)

Micro Flame Ionization Detector (µFID)

Micro Photo Ionization Detector (µPID)

Fast-scanning Mass Spectral Detector (MS)

Micro Electron Capture Detector (µECD)

Micro Flame Photometric Detector (µFPD)

Dual in line detectors (μTCD- μFID, μPID- μFID, μFID- μFPD, μTCD- μFPD)

Detection limits will depend on injector/detector combinations, but in general are about 10 ppb (by volume) for VOC's and about 10 ng injected for semivolatile organic compounds.

Performance

Quantitative determinations, repeatability of ±1%.

Retention times, repeatability of ±1%.

Analysis times for VOC's: 60 to 120 seconds.

Peak capacities for VOC's of 100 (RI 300 to 1000).

Analysis times for SVOC's: 60 to 240 seconds.

Peak capacities for SVOC's of 400 (RI 1000 to 3000).

Dynamic range: $10^4$, depending on the particular detector used.

As used in the claims below, the "temperature sensor" may comprise the heater, or it may be separate from the heater. In other words, the temperature sensor is not necessarily a physically separate element from the heater. In many instances, it may be desirable to have a single wire, tube, or other metallic element function both as an electrically resistive heater, and as an RTD in which the temperature is measured as a function of the resistance of the same wire.

All references cited in this specification are hereby incorporated in their entirety; provided that the present specification takes precedence in the event of any inconsistencies between it and such a reference.

We claim:

1. A gas chromatograph comprising:
   (a) an elongated or coiled heater;
   (b) an elongated or coiled analytical column, wherein at least about 80% of the length of said column is positioned substantially parallel to said heater, and wherein at least about 80% of the length of said column is within 5 millimeters of the nearest point of said heater;
   (c) a temperature sensor for measuring the temperature of said column or the temperature near said column; and
   (d) a microprocessor responsive to said temperature sensor to control said heater;
   wherein said chromatograph is adapted for controlled temperature programming of said column; and wherein said heater is adapted for controlled temperature programming of said column at a rate of power consumption less than about 110 Watts.

2. A chromatograph as recited in claim 1, wherein said chromatograph is adapted for controlled temperature programming of said column at a rate of at least about 0.5° C. per second.

3. A chromatograph as recited in claim 2, wherein said chromatograph is adapted for controlled temperature programming of said column at a rate of at least about 10° C. per second.

4. A chromatograph as recited in claim 3, wherein said chromatograph is adapted for controlled temperature programming of said column at a rate of at least about 25° C. per second.

5. A chromatograph as recited in claim 1, wherein the inner diameter of said column is less than about 270 microns.

6. A chromatograph as recited in claim 1, wherein said heater is adapted for controlled temperature programming of said column at a rate of power consumption less than about 100 Watts.

7. A chromatograph as recited in claim 1, wherein said chromatograph has a peak capacity of at least about 100 for compounds having elution times from said chromatograph between the elution time of propane and the elution time of n—$CH_3(CH_2)_{28}CH_3$.

8. A chromatograph as recited in claim 1, wherein said chromatograph has a peak capacity of at least about 500 for compounds having elution times from said chromatograph between the elution time of propane and the elution time of n—$CH_3(CH_2)_{28}CH_3$.

9. A chromatograph as recited in claim 1, wherein said chromatograph comprises a plurality of said columns.

10. A gas chromatograph comprising:
    (a) an elongated or coiled heater;
    (b) an elongated or coiled analytical column, wherein at least about 80% of the length of said column is positioned substantially parallel to said heater, and wherein at least about 80% of the length of said column is within 5 millimeters of the nearest point of said heater;
    (c) a temperature sensor for measuring the temperature of said column or the temperature near said column;
    (d) a microprocessor responsive to said temperature sensor to control said heater; and
    (e) an elongated or coiled tube; wherein said column is contained substantially within said tube; wherein said heater comprises said tube or wherein said heater is contained substantially within said tube, or wherein said heater comprises a thin conducting film on the interior of said tube where said tube is otherwise non-conducting; and wherein said heater does not comprise an electrically resistive film that adheres to the outside surface of said column over substantially the entire length of said column; and wherein said temperature sensor comprises said tube or wherein said temperature sensor is contained substantially within said tube;
    wherein said chromatograph is adapted for controlled temperature programming of said column.

11. A chromatograph as recited in claim 1, additionally comprising a cylindrical support comprised of a thermally insulating surface material, wherein said heater, said temperature sensor, and said column each lie substantially on or within the thermally insulating surface material.

12. A chromatograph as recited in claim 1, additionally comprising a source for flowing a sheath gas over said column to reduce thermal variations over the length of said column.

13. A chromatograph as recited in claim 1, additionally comprising a plurality of outlets from said column to direct analytes exiting said column to one or more of a plurality of detectors.

14. A sample processor for initial processing of a sample for analysis in a gas chromatograph prior to placing the sample in an analytical column of the chromatograph, said processor comprising:
    (a) an inlet for receiving the sample;
    (b) means for directing the sample from the inlet to a tube for temporarily holding the sample, without substantial backflow from the analytical column;
    (c) a retention gap connecting said temporary holding tube to the analytical column;
    (d) first carrier gas means for flowing a carrier gas through the temporary holding tube to transport the sample to said retention gap, and onto the analytical column;
    (e) second carrier gas means to direct a selected amount of the sample through the column, and to simultaneously backflush any remaining portion of the sample from said retention gap and away from the column; and (f) a microprocessor to control said first and second carrier gas means.

15. A sample processor as recited in claim 14, wherein said temporary holding tube comprises an open tube.

16. A sample processor as recited in claim 14, wherein said temporary holding tube comprises a sorbent-packed tube.

17. A sample processor as recited in claim 14, wherein said temporary holding tube is internally coated with a sorbent.

18. A sample processor as recited in claim 14, wherein said temporary holding tube comprises a tube adapted to be cryogenically cooled.

19. A sample processor as recited in claim 14, wherein said processor is adapted for temperature programming of said temporary holding tube at a rate of at least about 0.5° C. per second.

20. A sample processor as recited in claim 14, wherein said processor is adapted for controlled temperature programming of said temporary holding tube at a rate of at least about 10° C. per second.

21. A sample processor as recited in claim 14, wherein said processor is adapted for controlled temperature programming of said temporary holding tube at a rate of at least about 25° C. per second.

22. A sample processor as recited in claim 14, wherein said processor is adapted for independent controlled temperature programming of said temporary holding tube and of said retention gap.

23. A sample processor as recited in claim 14, wherein said processor comprises a plurality of said temporary holding tubes.

24. A sample processor as recited in claim 14, wherein said second carrier gas means additionally comprises a pressure control.

25. A sample processor as recited in claim 14, wherein said processor is adapted to transport the sample such that the sample never contacts a valve after the sample has entered said inlet.

26. A sample processor as recited in claim 14, wherein said second carrier gas means is additionally adapted to backflush any remaining portion of the sample from said temporary holding tube.

27. A sample processor as recited in claim 14, additionally comprising a vent adapted to allow said first carrier gas means to flush any remaining portion of the sample from said temporary holding tube through said vent.

28. A sample processor as recited in claim 14, additionally comprising a plurality of outlets from said retention gap to direct the sample exiting said retention gap to one or more of a plurality of analytical columns.

29. A sample processor as recited in claim 14, additionally comprising means for evaporating solvent or volatile sample components from the sample while the sample is in said temporary holding tube.

30. A sample processor as recited in claim 14, wherein said temporary holding tube comprises a phase to partition semi-volatile components of the sample from any volatile components of the sample, and additionally comprises means for flowing the volatile components from the temporary holding tube while the partitioned components from the sample are in the partitioning phase in said temporary holding tube.

31. A sample processor as recited in claim 14, wherein said second carrier gas means is adapted to reach its full operating pressure in a time less than about 20 msec.

32. A sample processor as recited in claim 14, wherein said sample processor is on a microchip.

33. A chromatograph comprising a sample processor as recited in claim 14, and additionally comprising:
   (a) an elongated or coiled heater;
   (b) an elongated or coiled analytical column, wherein at least about 80% of the length of said column is positioned substantially parallel to said heater, and wherein at least about 80% of the length of said column is within 5 millimeters of the nearest point of said heater;
   (c) a temperature sensor for measuring the temperature of said column or the temperature near said column; and
   (d) a microprocessor responsive to said temperature sensor to control said heater;
wherein said chromatograph is adapted for controlled temperature programming of said column.

34. A chromatograph as recited in claim 6, wherein said heater is adapted for controlled temperature programming of said column at a rate of power consumption less than about 50 Watts.

* * * * *